United States Patent
Roy et al.

(10) Patent No.: US 8,588,927 B2
(45) Date of Patent: Nov. 19, 2013

(54) IMPLANTABLE PULSE GENERATOR

(75) Inventors: Yves Roy, Beauport (CA); Eric Bharucha, Sainte-Foy (CA)

(73) Assignee: Neurostream Technologies General Partnership, Quebec (CA)

( * ) Notice: Subject to any disclaimer, the term of this patent is extended or adjusted under 35 U.S.C. 154(b) by 804 days.

(21) Appl. No.: 11/920,814

(22) PCT Filed: Oct. 9, 2007
(Under 37 CFR 1.47)

(86) PCT No.: PCT/CA2007/001787
§ 371 (c)(1),
(2), (4) Date: Apr. 28, 2010

(87) PCT Pub. No.: WO2008/049199
PCT Pub. Date: May 2, 2008

(65) Prior Publication Data
US 2010/0280577 A1    Nov. 4, 2010

Related U.S. Application Data

(60) Provisional application No. 60/849,839, filed on Oct. 6, 2006.

(51) Int. Cl.
*A61N 1/08* (2006.01)
(52) U.S. Cl.
USPC .......................................................... 607/62
(58) Field of Classification Search
USPC .......................................................... 607/62
See application file for complete search history.

(56) References Cited

U.S. PATENT DOCUMENTS

| 5,941,906 | A | 8/1999 | Barreras, Sr. |
| 6,544,171 | B2 | 4/2003 | Beetz et al. |
| 6,990,376 | B2 | 1/2006 | Tanagho et al. |
| 2004/0186526 | A1 | 9/2004 | Freeberg |
| 2004/0210270 | A1 | 10/2004 | Erickson |
| 2004/0230231 | A1 | 11/2004 | Thacker et al. |
| 2005/0278001 | A1 | 12/2005 | Qin et al. |
| 2006/0247739 | A1* | 11/2006 | Wahlstrand et al. ............ 607/62 |

FOREIGN PATENT DOCUMENTS

WO    2006118773 A1    11/2006

* cited by examiner

*Primary Examiner* — Eric D. Bertram
(74) *Attorney, Agent, or Firm* — Polsinelli PC

(57) ABSTRACT

An implantable pulse generator for providing at least one of a voltage and a current stimulation to a tissue of a subject through trough at least two electrodes adapted to be in electrical contact with the tissue of the subject, the implantable pulse generator comprising a stimulation circuit coupled to the at least two electrodes, the stimulation circuit including at least one dual-mode voltage and current source, wherein the stimulation circuit can operate alternatively in a voltage stimulation mode and in a current stimulation mode. The implantable pulse generator also comprises a processing unit coupled to the stimulation circuit, the processing unit being so configured as to control the mode of operation of the stimulation circuit. The implantable pulse generator may also comprise a monitoring unit coupled to the stimulation circuit and the processing unit; the monitoring unit being so configured as to provide feedback signals relating to electrical characteristics of the tissue from the stimulation circuit to the processing unit.

3 Claims, 11 Drawing Sheets

US 8,588,927 B2

IMPLANTABLE PULSE GENERATOR

CROSS-REFERENCE TO RELATED APPLICATION

This application is a U.S. National Phase of International Patent Application No. PCT/CA2007/001787, filed Oct. 9, 2007 which claims priority to U.S. Patent Application No. 60/849,839 filed Oct. 6, 2006.

TECHNICAL FIELD

The present invention relates to an implantable pulse generator. More specifically, the present invention relates to an implantable pulse generator for providing current and/or voltage stimulation signals to muscles, nerves or tissue.

BACKGROUND

The use of implantable pulse generators (IPG) for providing therapeutic electrical signals may provide advantageous effects to subjects who present physiological disorders that may be mitigated or circumvented by the use of stimulating current or voltage waveforms. While there are systems that perform well at this task by making use of either controlled-current signals or controlled-voltage signals, these systems do not offer the flexibility of being able to generate both types of stimulating waveforms. Having a single type of types of stimulating waveforms per IPG means that multiple IPGs would have to be implanted whenever a multi-therapy treatment is required.

SUMMARY

According to an illustrative embodiment of the present invention, there is provided an implantable pulse generator for providing at least one of a voltage and a current stimulation to a tissue of a subject through at least two electrodes adapted to be in electrical contact with the tissue of the subject. The implantable pulse generator comprises a stimulation circuit coupled to the at least two electrodes, the stimulation circuit including at least one dual-mode voltage and current source, wherein the stimulation circuit can operate alternatively in a voltage stimulation mode and in a current stimulation mode, and a processing unit coupled to the stimulation circuit, the processing unit being so configured as to control the mode of operation of the stimulation circuit.

According to a another illustrative embodiment of the present invention, the implantable pulse generator further comprises a monitoring unit coupled to the stimulation circuit and the processing unit; the monitoring unit being so configured as to provide feedback signals relating to electrical characteristics of the tissue from the stimulation circuit to the processing unit.

According to a further illustrative embodiment of the present invention, there is provided a dual-mode voltage and current source, comprising:
an operational amplifier having a positive input, a negative input and an output;
a first feedback resistor connected between the negative input of the operational amplifier and a ground;
a differential amplifier having a positive input connected to the output of the operational amplifier, a negative input and an output;
a sensing resistor connected between the negative and positive inputs of the differential amplifier;
a mode selection switch having a first connection connected to the output of the differential amplifier, second connection connected to the negative input of the differential amplifier and a third connection;
a second feedback resistor connected between the negative input of the operational amplifier and the third connection of the mode selection switch; and
a source output connected to the negative input of the differential amplifier;
wherein a) when the mode selection switch connects the second feedback sensor to the negative input of the differential amplifier, the source output generates a voltage stimulation, and b) when the mode selection switch connects the second feedback resistor to the output of the differential amplifier, the source output generates a current stimulation.

According to a still further illustrative embodiment of the present invention, there is provided a dual-mode voltage and current source, comprising:
an operational amplifier having a positive input, a negative input and an output;
a first feedback resistor connected between the negative input of the operational amplifier and one of a ground and a power source;
a saturation transistor having a gate connected to the output of the operational amplifier, a sink and a drain;
a sensing resistor connected between the drain of the saturation transistor and the one of a ground and a power source;
a saturation switch connected between the negative input of the operational amplifier and the one of a ground and a power source;
a second feedback resistor connected between the negative input of the operational amplifier and the drain of the saturation transistor;
a voltage source having an output;
a voltage source switch connected between the output of the voltage source and the sink of the saturation transistor,
a source output connected to the sink of the saturation transistor;
wherein a) when the voltage source switch is closed and the saturation switch is open, the source output generates a voltage stimulation, and b) when the voltage source switch is open and the saturation switch is closed, the source output generates a current stimulation.

BRIEF DESCRIPTION OF THE FIGURES

Embodiments of the invention will be described by way of example only with reference to the accompanying drawings, in which.

DEFINITIONS

The detailed description and figures refer to the following terms which are herein defined:

Electrode: any interface such as, for example, an electrode, a lead, a probe, a nerve cuff, etc., that may be used to electrically connect a device to a tissue.

Tissue: any biological tissue such as, for example, muscle, nerve, etc., that may benefit from therapeutic electrical signals.

DETAILED DESCRIPTION

Generally stated, non-limitative illustrative embodiments of the present invention overcome the deficiencies of the prior art implantable pulse generators (IPG) by providing an IPG which can provide current and/or voltage stimulation signals to tissues of a subject. This is particularly of interest as it precludes using more than one IPG when both current stimulation and voltage stimulation are required, or may be required in the future, to dispense treatment.

Figure 1:
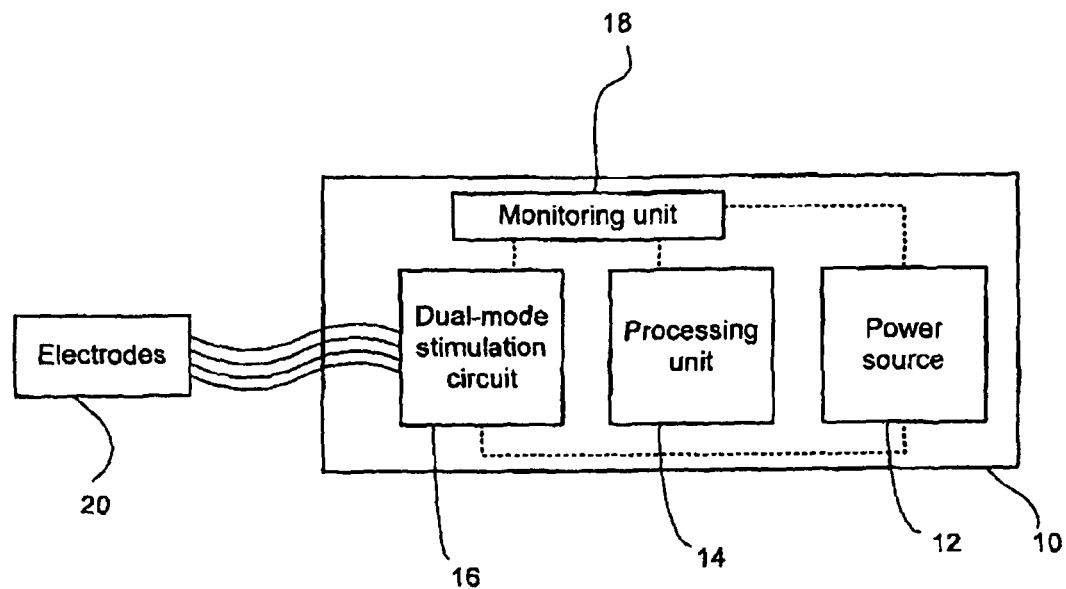
FIG. 1 is a block diagram of an implantable pulse generator according to an illustrative embodiment of the present invention.

To this end, with reference to FIG. 1, an IPG 10 includes a power source 12 that feeds a processing unit 14, which in turn controls at least one dual-mode stimulation circuit 16 that may be connected to at least two electrodes 20 (or channels on a nerve cuff) adapted to be connected to tissues of a subject (not shown). The IPG 10 also includes a monitoring unit 18, which provides feedback signals that relate to the tissue's electrical characteristics from the dual-mode stimulation circuit 16 to the processing unit 14 in order to adjust the stimulation provided by the dual-mode stimulation circuit 16.

As opposed to the prior art, the dual-mode stimulation circuit 16 may be independently programmed to output various voltage waveforms at various amplitudes, thus also giving the IPG 10 the capability to perform voltage steering during stimulation. The processing unit 14 is used to program, charge and control the dual-mode stimulation circuit 16.

Since impedance measurements imply voltage measurements when current stimulation is performed and current measurements when voltage stimulation takes place, the monitoring unit 18 may monitor the required signals to provide impedance measurements. This allows the IPG 10 to measure impedance for both types of stimulation waveforms.

Alternatively, the power may be supplied transcutaneously from an external power generator to the IPG 10 using, for example, inductive coupling between two coils. In this case, the power source 12 may be, for example, a coil with associated circuitry.

Figure 2:
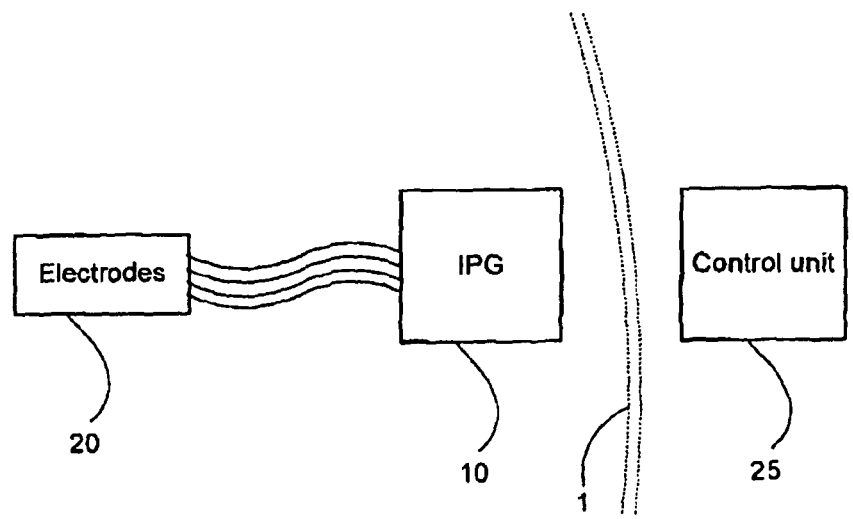
FIG. 2 is a block diagram of a system using the implantable pulse generator of FIG. 1.

Referring to FIG. 2, the IPG 10, together with the electrodes 20 may implanted below the skin 1 of a subject and may communicate with an external control unit 25 that may be used to configure and/or monitor the operation of the IPG 10.

Alternatively, in the case where the IPG 10 power is provided transcutaneously, the external control unit 25 may be provided with a power generator, coil and associated circuitry so as to transmit power to the power source 12 through the skin of the subject.

Single-Mode Stimulation Circuit

Figure 3:
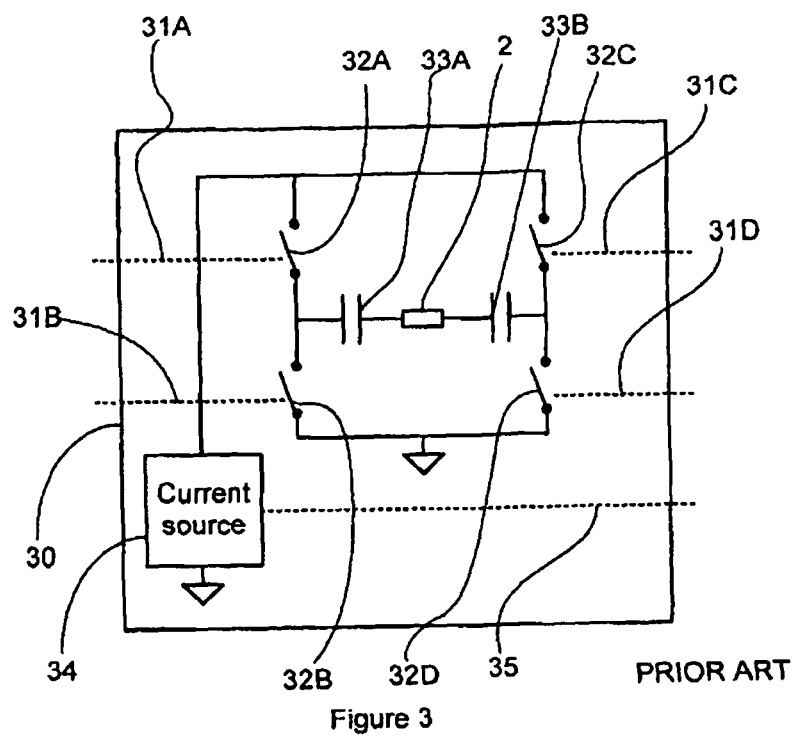
FIG. 3 is a block diagram of a prior art H-bridge based current stimulation circuit.
Figure 4:
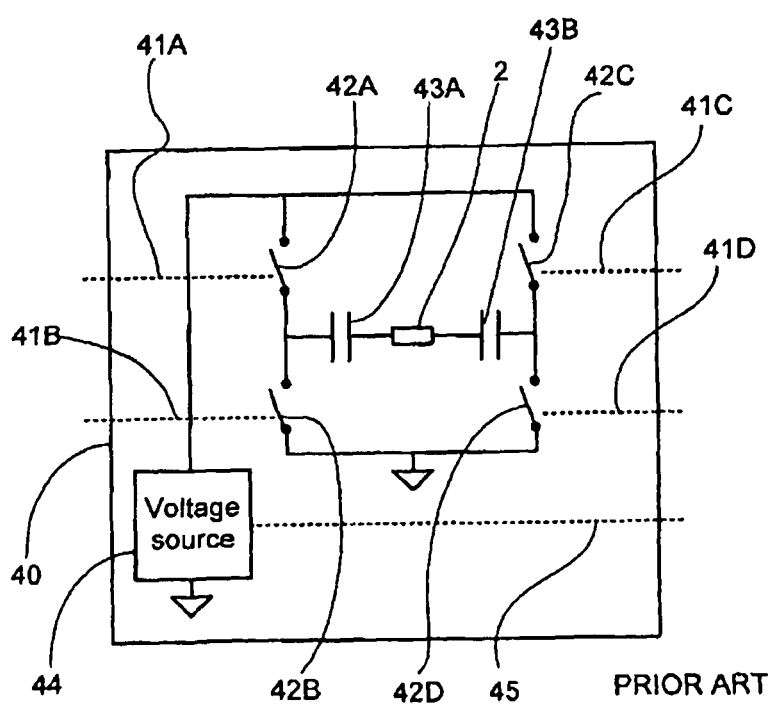
FIG. 4 is a block diagram of a prior art H-bridge based voltage stimulation circuit.

Referring to FIGS. 3 and 4, prior art designs of single-mode stimulation circuits 30 and 40 commonly make use of H-bridge based current or voltage sources, respectively, to generate biphasic therapeutic stimulation waveforms. The single-mode stimulation circuits 30 and 40 may also be used to produce unipolar waveforms, but in this case simpler circuits may be used in to reduce the complexity of the associated IPG.

In FIG. 3, a control circuit (not shown) is used to control single-mode stimulation circuit 30 such that the control signal lines 31A and 31D close or open associated switches 32A and 32D while the control signal lines 31B and 31C open or close associated switches 32B and 32C. The configuration signal line 35 is used to set the current level the current source 34 outputs. In some cases, the configuration signal line 35 carries digital control signals produced by the processing unit of the IPG (not shown). In other cases, the configuration signal line 35 carries an analog signal which sets the value of the current the source 34 outputs.

In such a configuration, it is important to avoid having the control signal lines 31A and 31B or 31C and 31D activate their associated switches 32A and 32B or 32C and 32D at the same time, which would result in the shorting of the output of the current source 34 and cause unnecessary current to flow, thus wasting energy. On the other hand, the control signal lines 31B and 31D may be both safely used to activate their respective switches 32B and 32D to discharge the blocking capacitors 33A and 33B and the stray capacitance of the tissue 2. Similarly, control signal lines 31A and 31C may both safely be used to activate their respective switches 32A and 32C to discharge the blocking capacitors 33A and 33B and the stray resistance/capacitance of the tissue 2. In practice, common IPGs may use multiple pairs of electrodes to provide a treatment, in which case the same number of single-mode stimulation circuits 30 would be required. Alternatively, the same number of H-bridges may be used with a shared current source 34.

The single-mode stimulation circuit 40 shown in FIG. 4 is obtained by replacing the current source 34 shown in FIG. 3 by a programmable voltage source 44. Instead of having a controlled current to flow in the tissue 2, it is a controlled voltage which is applied across the tissue 2. Apart from that, the operation of the single-mode stimulation circuit 40 shown in FIG. 4 is similar to the one of the single-mode stimulation circuit 30 shown in FIG. 3, the control signal lines 41A, 41B, 41C, 41D, with associated switches 42A, 42B, 42C, 42D, blocking capacitors 43A, 43B and configuration signal line 45 behaving in a similar fashion as in the case of single-mode stimulation circuit 30. Both single-mode stimulation circuits 30 and 40 do not require fast responsive sources 34, 44 that consume more power to invert the direction of the current that flows in the tissue 2, as this task is managed by the much more power efficient H-bridge based circuits.

Although the single-mode stimulation circuits 30 and 40 shown in FIGS. 3 and 4, respectively, share similar architectures, they are not interchangeable because of the sources 34, 44 they use. Their use is thus limited by the type of stimulation they can provide.

Dual-Mode Stimulation Circuit

Figure 5:
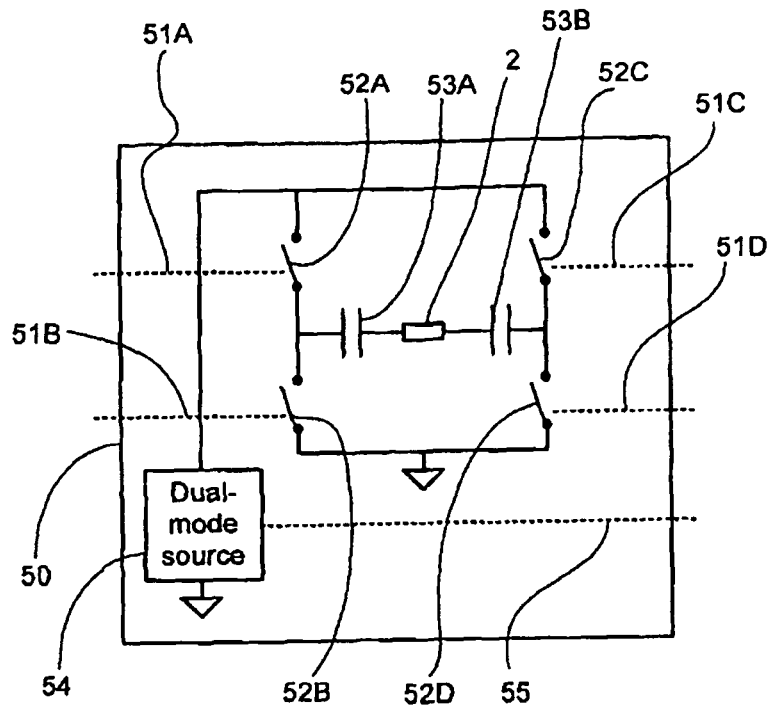
FIG. 5 is a block diagram of a first illustrative embodiment of the dual-mode stimulation circuit of FIG. 1.

Referring now to FIG. 5, there is shown a block diagram of a dual-mode stimulation circuit 50 according to a first illustrative embodiment of the dual-mode stimulation circuit 16 of FIG. 1. The dual-mode stimulation circuit 50 shares some common features with the single-mode stimulation circuits 30 and 40 shown in FIGS. 3 and 4, respectively, namely control signal lines 51A, 51B, 51C, 51D with associated switches 52A, 52B, 52C, 52D, blocking capacitors 53A, 53B and configuration signal line 55, with the exception that the current source 34 and voltage source 44 are replaced by a dual-mode source 54. The dual-mode source 54 may be configured to output a programmable current or voltage level using the configuration signal line 55. This capability of sourcing either current or voltage is an advantage over the prior art as this allows the production of a single IPG 10 having the capability of providing treatment in either mode of operation, i.e. a current or voltage based treatment. A dual-mode source that may be used for the dual-mode source 54 will be detailed further on.

This capability of switching at will from one mode of operation to the other instead having to surgically remove a prior art IPG operating in a given mode from a subject's body to replace it with another prior art IPG operating in another mode is desirable as it opens the way to treatments that advantageously combine the benefits of stimulating current and voltage waveforms to better adapt itself to the evolution of the response of the tissue 2 to the therapeutic waveforms. Furthermore, the capability to control either the current level or the voltage level of the waveforms the dual-mode source 54 outputs allows impedance measurements that are based on these two types of signals as opposed to what can be done with a single-mode source 34, 44. This capability to evaluate the same characteristics with two different methods is another advantage over prior art single-mode stimulation circuits 30 and 40 as the comparison of the results obtained may allow the detection of discrepancies that might have otherwise been undetected.

Although the dual-mode stimulation circuit 50 of FIG. 5 includes a single dual-mode source 54, it is to be understood that the dual-mode stimulation circuit 50 may include a plurality of H-bridges with multiple dual-mode sources 54 to provide even more flexibility than what is achieved by the current single-mode stimulation circuits 30, 40. Thus, a first group of dual-mode sources 54 may be configured to provide current stimulation, while a second group may be configured to generate stimulating voltage signals. In such cases, a single IPG 10 may advantageously be used to administrate a plurality of treatments that may have otherwise required the use of many prior art single-mode IPGs. Furthermore, the capability to individually configure the output level and the output mode of each dual-mode source 54 of such embodiments enables multi-mode steering of the resulting treatment.

A second illustrative embodiment 60 of the dual-mode stimulation circuit 16 of FIG. 1 is shown in FIG. 6, which again shares a similar architecture with the single-mode stimulation circuits 30 and 40 of FIGS. 3 and 4, respectively, namely control signal lines 61A, 61B, 61C, 61D, with associated switches 62A, 62B, 62C, 62D and blocking capacitors 63A, 63B, with the exception that the current source 34 and voltage source 44 are replaced by a pair of dual-mode sources 64A and 64B having respective configuration signal lines 65A and 65B. The architecture of the dual-mode stimulation circuit 60 further differs from that of single-mode stimulation circuits 30 and 40 in that each pair of switches (62A, 62B) and (62C, 62D) connect to the same end of a load formed by the blocking capacitors 63A, 63B and the tissue 2 and are fed by an associated dual-mode source 64A, 64B, respectively, thus forming branches 66A and 66B. A dual-mode source that may be used for the dual-mode sources 64A and 64B will be detailed further on.

Figure 6:
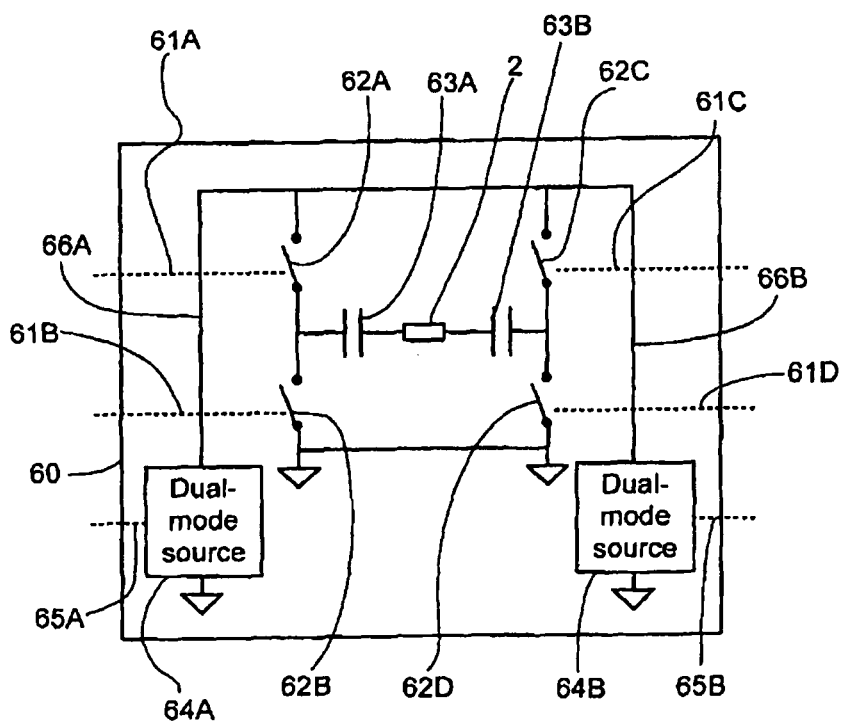
FIG. 6 is a block diagram of a second illustrative embodiment of the dual-mode stimulation circuit of FIG. 1.

FIG. 6 only shows two branches 66A, 66B for clarity but other embodiments of the dual-mode stimulation circuit 60 may include multiple branches. The configuration shown in FIG. 6 leads to a dual-mode stimulation circuit 60 architecture which is more complex than that of the dual-mode stimulation circuit 50 shown in FIG. 5 since two dual-mode sources 64A, 64B are required to drive the same number of switches 62A, 62B, 62C, 62D. However, the advantages that result from the split of the H-bridge into branches 66A, 66B is more evident when multiple branches are considered so as to allow steering of the produced stimulation. Thus, it results from the use of the two dual-mode sources 64A, 64B that the outputs of the dual-mode stimulation circuit 60, which are in contact with tissue 2, may be independently controlled instead of being coupled to each other as it is the case where a single dual-mode source controls these outputs. The dual-mode sources 64A and 64B will be detailed further on.

Figure 7:
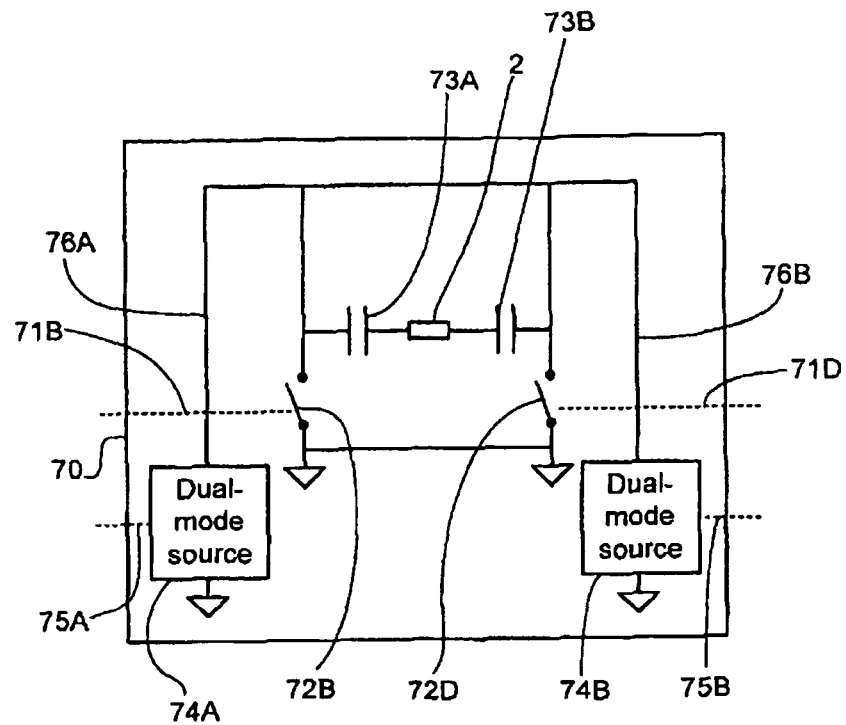
FIG. 7 is a block diagram of a third illustrative embodiment of the dual-mode stimulation circuit of FIG. 1.

A third illustrative embodiment 70 of the dual-mode stimulation circuit 16 of FIG. 1 is shown in FIG. 7, which is derived from the dual-mode stimulation circuit 60 of FIG. 6, having similar components, namely control signal lines 71B, 71D, with associated switches 72B, 72D, blocking capacitors 73A, 73B, dual-mode sources 74A, 74B and configuration signal lines 75A, 75B, with the exception of the top most switches 62A and 62C being replaced by short circuits. A dual-mode source that may be used for the dual-mode sources 74A and 74B will be detailed further on.

This dual-mode stimulation circuit 70 is less complex than dual-mode stimulation circuits 50 and 60 as it only includes one switch 72B and 72D per branch, respectively, instead of two, i.e. (62A, 62B) and (62C, 62D). To preserve the functionality of the dual-mode stimulation circuit 70, the control of the operation of its sources 74A and 74B must compensate for the removal of the switches, i.e. 62A and 62C. A current source, when not outputting a current, is seen by the load it is connected to as if it was an open circuit. Hence, the dual-mode stimulation circuit 70 of FIG. 7 may generate the same therapeutic stimulation signals as the dual-mode stimulation circuit 60 of FIG. 6 provided that the configuration signal line 75B is such that dual-mode source 74B operates as a current source that outputs no current each and every time the control signal line 71D forces the opening of the switch 72D. Conversely, configuration signal line 75A should be such that dual-mode source 74A operates as a current source that outputs no current each and every time the control signal line 71B forces the opening of the switch 72B.

Alternative embodiments of dual-mode stimulation circuit 70 of FIG. 7 may include more branches 76A, 78B than shown in FIG. 7 in order to provide the same flexibility and the same advantages as mentioned above for stimulation circuits based on the dual-mode stimulation circuit 60 of FIG. 6.

Figure 8:
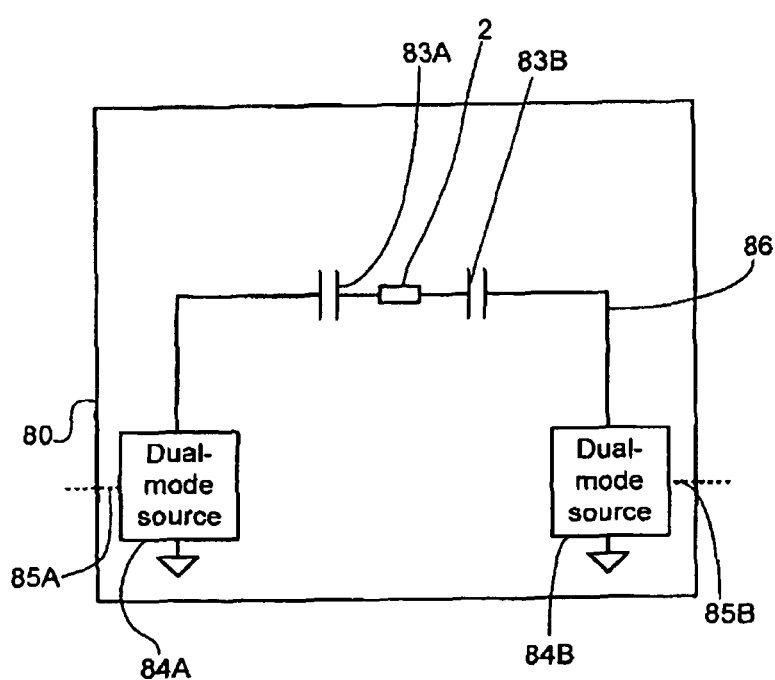
FIG. 8 is a block diagram of a fourth illustrative embodiment of the dual-mode stimulation circuit of FIG. 1.

A fourth illustrative embodiment 80 of the dual-mode stimulation circuit 16 of FIG. 1 is shown in FIG. 8, which includes dual-mode sources 84A, 84B and blocking capacitors 83A, 83B, but no switches. A dual-mode source that may be used for the dual-mode sources 84A and 84B will be detailed further on.

A voltage source that produces zero volts across its outputs is seen as a short circuit by the load it connects to. Hence, the dual-mode stimulation circuit 80 of FIG. 8 may produce the same therapeutic stimulation signals as the dual-mode stimulation circuit 70 of FIG. 7 provided that the configuration signal line 85B is such that the dual-source source 84B operates as a voltage source that outputs zero volt each and every time the dual-source 84A is configured to output current or voltage waveforms. Conversely, the configuration signal line 85A should be such that the dual-mode source 84A acts as a voltage source that outputs zero volts whenever the dual-source 84B is configured to output current or voltage waveforms.

If the dual-mode sources 84A, 84B are configured so as to sink or source current when they act as current sources, the dual-mode stimulation circuit 80 is not limited to situations for which a dual-mode source 84A, 84B has to be configured to output zero volts when the other dual-mode source 84A, 84B is active, provided that the currents that enter the dual-mode source 84A, 84B add up to zero at all time. Thus, multiple combinations of mode of operation may be used to produce stimulation signals. For example, having a dual-mode source 84A, 84B that outputs 3 V while the other sinks 20 mA of current would be a possible configuration. On the other hand, making a dual-mode source 84A, 84B sink 20 mA whilst the other is asked to output 30 mA would not be feasible since more current would be entering the tissue 2 than out of it, i.e. the currents that enter the dual-mode source 84A, 84B add up to 10 mA. The processing unit 14 of the IPG 10 of FIG. 1 may be programmed to prevent improper configuration of the dual-mode source 84A, 84B.

Since it is possible to control the output voltage of a given dual-source 84A or 84B of the stimulation circuit 80 while the other dual-source 84B or 84A acts as a current source, it becomes possible to minimize the voltage across that current source as it stimulates the tissue 2. The stimulation circuit 80 thus allows power consumption reduction if the processing unit 14 of the IPG 10 of FIG. 1 is also programmed to minimize the voltage across its dual-mode sources 84A, 84B when they act as current sources.

Alternative embodiments of dual-mode stimulation circuit 80 of FIG. 8 may include more branches 86 than shown in FIG. 8 in order to provide the same flexibility and the same advantages as mentioned above for stimulation circuits based on the dual-mode stimulation circuit 70 of FIG. 7.

Figure 9:
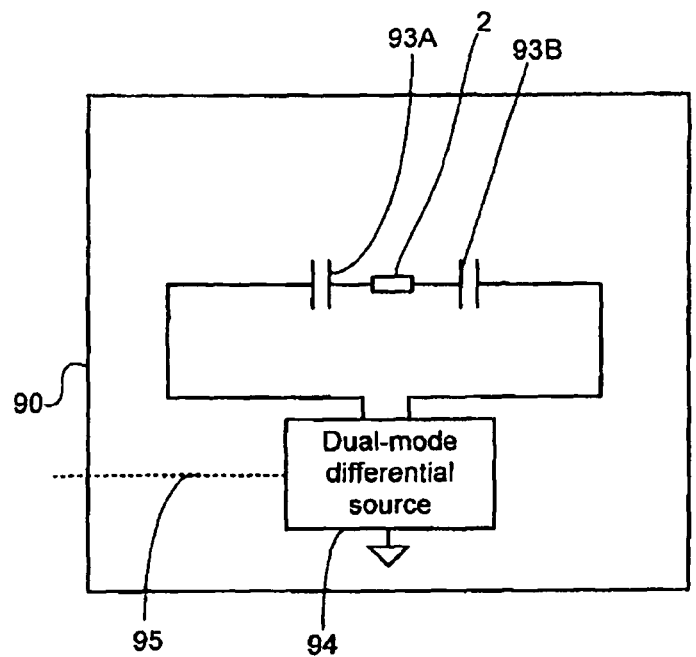
FIG. 9 is a block diagram of a fifth illustrative embodiment of the dual-mode stimulation circuit of FIG. 1.

A fifth illustrative embodiment 90 of the dual-mode stimulation circuit 16 of FIG. 1 is shown in FIG. 9, which may be used when only a single therapeutic signal is required. The dual-mode stimulation circuit 90 makes use of a single dual-mode differential source 94 that may either operate as a differential current source or as a differential voltage source, along with blocking capacitors 93A, 93B. Because of the differential nature of the source 94, there is no need to control the direction of the current when the polarity of the output signal has to change.

Since the dual-mode stimulation circuit 90 includes a single dual-source differential source 94 and no switch, a simplified version of the processing unit 14 of FIG. 1 may be used to produce the configuration signal line 95 signals used to control the dual-mode differential source 94. The configuration signal line 95 only has to control the modes of operation and the output level of the dual-mode differential source 94. When the dual-mode stimulation circuit 90 is required to produce a multitude of stimulating signals and/or if steering capabilities are expected, an alternative embodiment that includes multiple dual-mode differential sources 94 may be used.

It should be noted that the purpose of the blocking capacitors 33A, 33B, 43A, 43B, 53A, 53B, 63A, 63B, 73A, 73B, 83A, 83B, 93A and 93B is to prevent DC leakage into the tissue.

Dual-mode Source and Other Circuits

Figure 10:
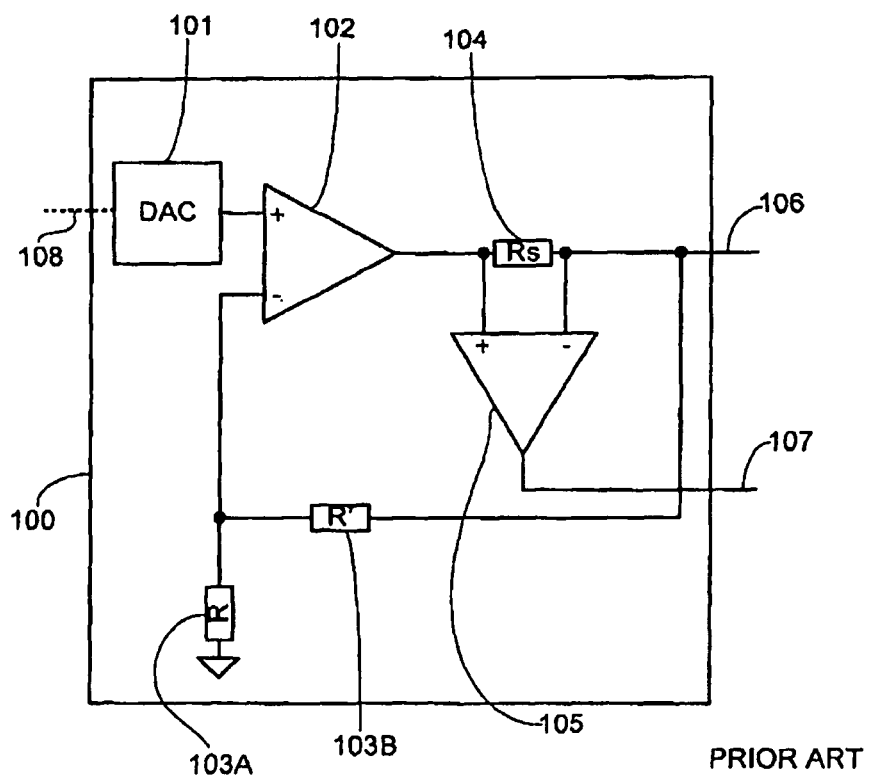
FIG. 10 is a block diagram of a prior art voltage source with current feedback.

Referring to FIG. 10, there is shown a block diagram of a prior art voltage source 100 with current feedback. A digital-to-analog converter (DAC) 101, controlled by configuration signal line 108, feeds the positive input of an inverting amplifier formed by operational amplifier 102, feedback resistors 103A, 103B and sensing resistor 104. Provided that the value of the sensing resistor 104 is kept small when compared to the output impedance of the differential amplifier 105, the impact of the sensing resistor 104 on the performances of the voltage source 100 is minimized because the feedback signal originates from its output 106.

Since the voltage across the sensing resistor 104 is proportional to the current delivered by the voltage source 100, having a differential amplifier 105 measure the voltage across the sensing resistor 104 enables impedance measurements of the load which is connected to the voltage source 100 that are based on the ratio of the recorded voltages 106 and 107. The voltage source 100 can either sink or source current. It is to be understood that in the preceding description of the impedance measurements it was assumed that the output 106 was connected to grounded tissue. If this is not the case, then the voltage at output 106 is to be replaced by the voltage drop across the stimulated tissue.

Figure 11:
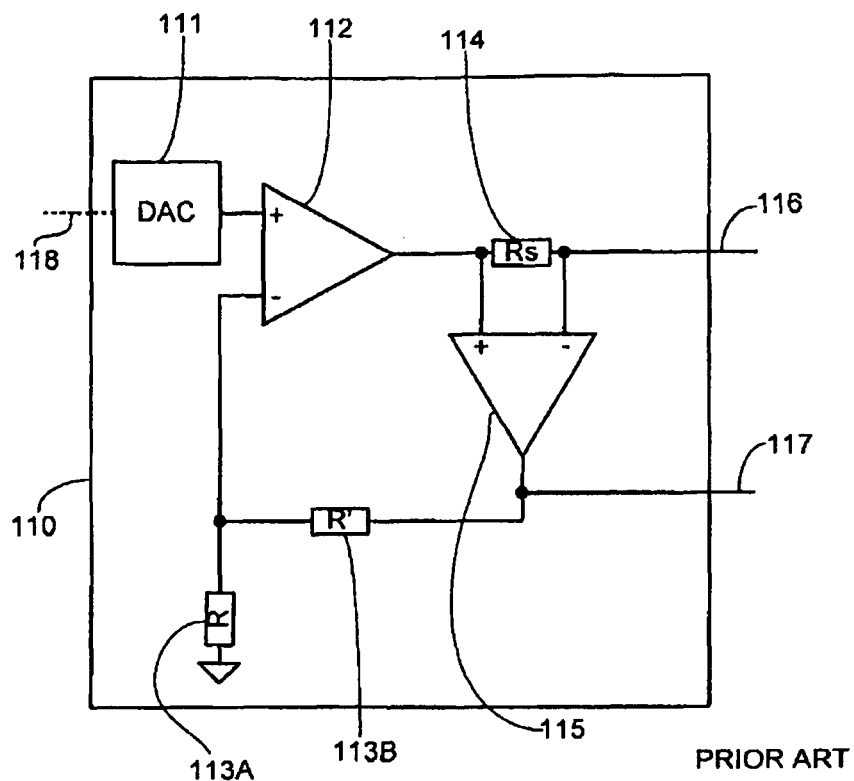
FIG. 11 is a block diagram of a prior art current source.

Referring to FIG. 11, there is shown a block diagram of a prior art current source 110. A DAC 111, controlled by configuration signal line 118, feeds the positive input of an inverting amplifier formed by operational amplifier 112, feedback resistors 113A and 113B, sensing resistor 114 and differential amplifier 115. Provided that the value of the sensing resistor 114 is kept small when compared to the output impedance of the differential amplifier 115, the impact of the sensing resistor 114 performances of the current source 110 is minimized since the feedback signal originates its output 116. The operational amplifier 112 thus performs current regulation because the feedback signal it processes is proportional to the output current of the current source 110.

Furthermore, since the voltage across the sensing resistor 114 is proportional to the current delivered by the current source 110, having the differential amplifier 115 measure the voltage across the sensing resistor 114 enables impedance measurements of the load which is connected to the current source 110 that are based on the ratio of the recorded voltages 116 and 117. The current source 110 can either sink or source current. It is to be understood that in the preceding description of the impedance measurements it was assumed that the output 116 was connected to grounded tissue. If this is not the case, then the voltage at output 116 is to be replaced by the voltage drop across the stimulated tissue.

Figure 12:
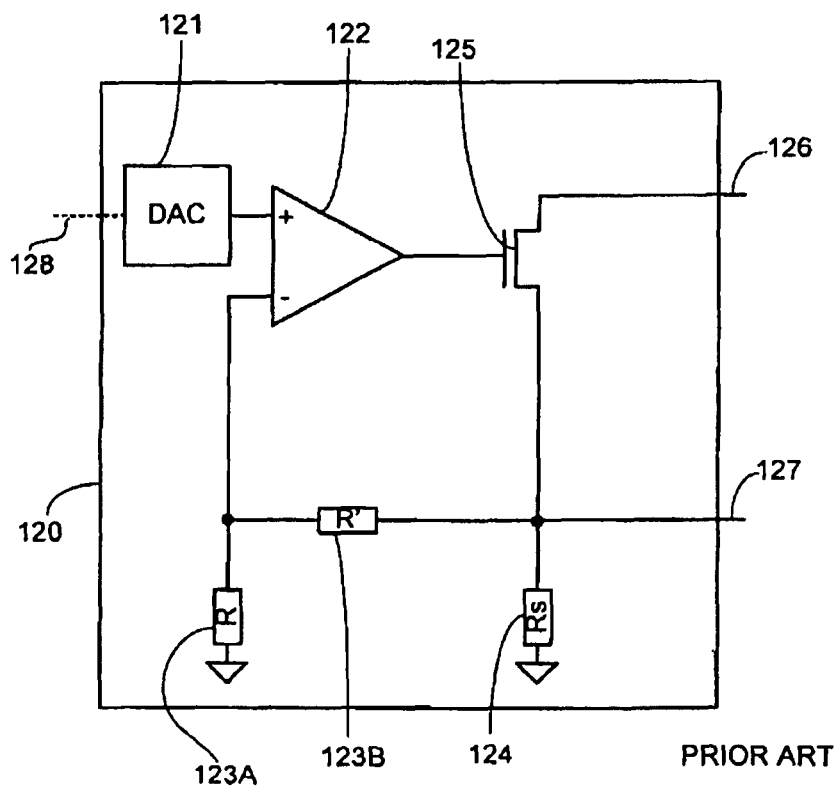
FIG. 12 is a block diagram of a prior art unidirectional current source.

Referring to FIG. 12, there is shown a block diagram of a prior art unidirectional current source 120. A DAC 121, controlled by configuration signal line 128, feeds the positive input of a voltage-to-current converter formed by operational amplifier 122, feedback resistors 123A and 123B, sensing resistor 124 and transistor 125. Provided that the values of the feedback resistors 123A and 123B are kept large when compared to the value of the sensing resistor 124, the impact of the feedback resistors 123A and 123B on the performances of the unidirectional current source 120 is minimized since this makes the current that flows in the sensing resistor 124 practically equal to the current the unidirectional current source 120 sinks. In order to have both of its inputs at the same voltage, the operational amplifier 122 will drive the gate of the transistor 125 in a way that forces a current proportional to the output of the DAC 121 to flow from the output 126 of the unidirectional current source 120 through the sensing resistor 124.

Since the voltage across the sensing resistor 124 is proportional to the current the unidirectional current source 120 sinks, the measure of both the voltage across the sensing resistor 124 and the voltage at the output 126 of the unidirectional current source 120 enables impedance measurements of the load which is connected to the unidirectional current source 120 that are based on the ratio of the recorded voltages 126 and 127.

Although the transistor 125 is shown to be a NMOS transistor in FIG. 12, a NPN transistor or equivalent may be used as well to implement the unidirectional current source 120. More specifically, since the unidirectional current source 120 may only make the current flow from its terminal 146 to the ground, a PMOS, a NPN transistor or an equivalent circuit may be used for the transistor 125 if there is a need to output current from the terminal 146, provided that the feedback resistors 123A, 123B and the sensing resistor 124 are connected to the power supply of the circuit instead of being connected to the ground.

Comparing the circuits of voltage source 100 and current source 110 shown in FIGS. 10 and 11, respectively, reveals a common architecture, apart from where the feedback is taken, which may be used as a basis for the dual-mode source.

Figure 13:
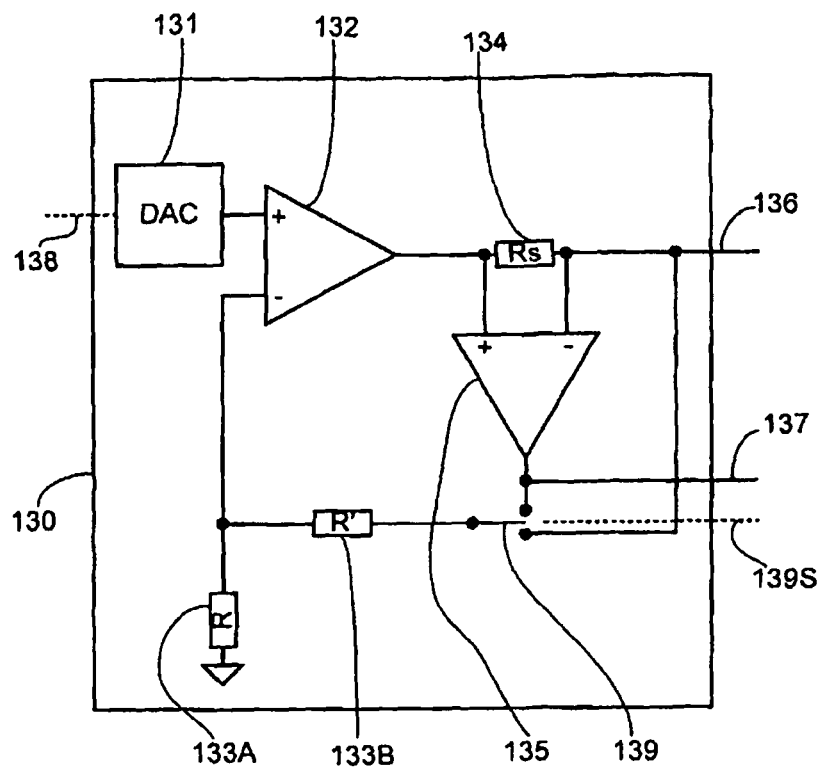
FIG. 13 is a block diagram of a dual-mode source.

Referring now to FIG. 13, there is shown block diagram of a dual-source 130 that may be used for dual-mode sources 54, 64A, 64B, 74A, 74B, 84A and 84B of FIGS. 5, 6, 7 and 8. A DAC 131, controlled by configuration signal line 138, feeds the positive input of a voltage-to-current converter formed by operational amplifier 132, feedback resistors 133A and 133B, sensing resistor 134 and differential amplifier 135. The processing unit 14 of the IPG 10, shown in FIG. 1, may control the mode of dual-source 130, i.e. current or voltage source mode, using the mode selection signal line 139S, which toggles the mode selection switch 139 to obtain either of the voltage or current source configurations shown in FIGS. 10 and 11, respectively. The current source mode is selected when the switch 139 is connected to the output of the differential amplifier 135 while the voltage mode is selected when the switch 139 is connected to the output 136 of the dual-mode source 130.

Since the voltage across the sensing resistor 134 is proportional to the current delivered by the dual-source 130, having a differential amplifier 135 measure the voltage across the sensing resistor 134 enables impedance measurements of the load which is connected to the dual-source 130 that are based on the ratio of the recorded voltages 136 and 137. The dual-mode source 130 may either sink or source current. It Is to be understood that in the preceding description of the impedance measurements it was assumed that the output 136 was connected to grounded tissue. If this is not the case, then the voltage at output 136 is to be replaced by the voltage drop across the stimulated tissue.

In an alternative embodiment, with reference to FIGS. 6, 7 and 8, the use of two dual-mode sources 64A, 64B, 74A, 74B, 84A and 84B may not be required for some applications. For example, an application may push current or voltage from one of the dual-mode source 64A, 64B, 74A, 74B, 84A and 84B (for example in a diagnostic mode) and replace the other one with a simple current source such as, for example, the unidirectional current source 120 of FIG. 12, for stimulation in order to provide better power performance. Thus, a dual-mode source allows the identification of the ideal therapy and another source, having a simpler circuit, provides stimulation while also providing power economy.

In a further alternative embodiment, with reference still to FIGS. 6, 7 and 8, each pair of dual-mode sources 64A, 64B, 74A, 74B, 64A and 84B may be replaced, respectively, by a voltage source and a current source. The voltage source and current source may be controlled by the processing unit 14 in order to provide either or both voltage and current stimulation.

It is to be understood that, although the preceding alternative embodiments make reference to the dual-mode stimulation circuits 60, 70 and 80 of FIGS. 6, 7 and 8, which respectively include two dual-mode sources 64A, 64B, 74A, 74B, 84A and 84B, the alternative embodiments may also apply to dual-mode stimulation circuits having a plurality of dual-mode sources and that the number of voltage and current sources need not be equal.

Figure 14:
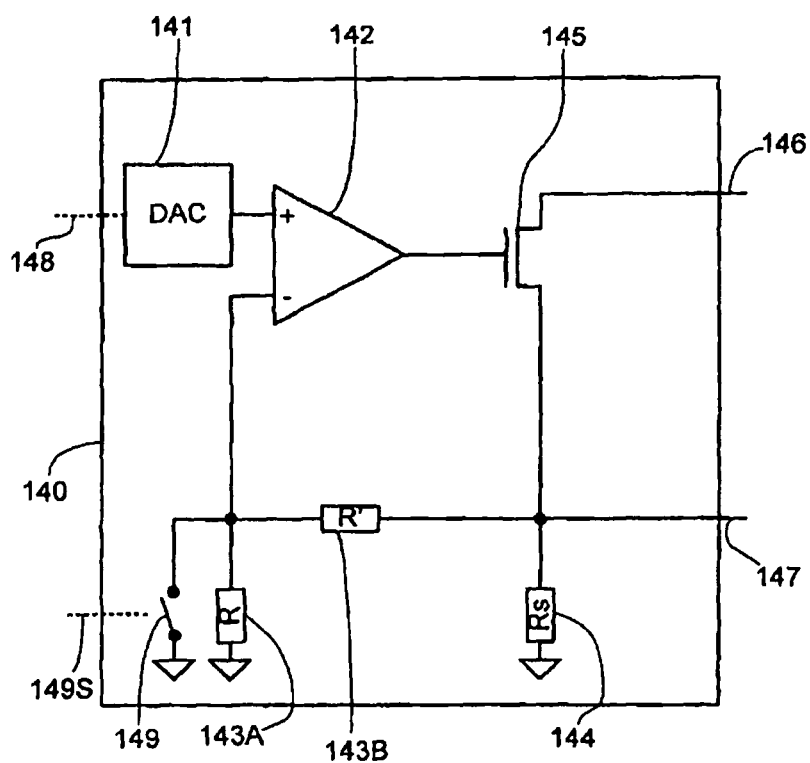
FIG. 14 is a block diagram of a saturable current source.

Referring to FIG. 14, there is shown a block diagram of a saturable current source 140 which includes a DAC 141, controlled by configuration signal line 148, feeding the positive input of a voltage-to-current converter formed by operational amplifier 142, feedback resistors 143A and 143B, sensing resistor 144 and transistor 145.

When switch 149 is open, the saturable current source 140 operates similarly to the unidirectional current source 120 of FIG. 12. However, when the saturation control signal line 149S causes the saturation switch 149 to be closed, the operational amplifier 142 does not receive any more feedback signals and its output reaches its positive supply rail because of its very high gain. This output being connected to the gate of the transistor 145, the high voltage value it produces when the switch 149 is closed causes saturation of the transistor 145. This make the transistor 145 behave like a low value resistor which is in series with the sensing resistor 144. Provided that the implementation of the saturable current source 140 is such that its output impedance is sufficiently low when the switch 149 is closed, the saturable current source 140 may be seen to be as a current source in parallel with a switch. This offers the advantage of making use of a simple low power control switch 149 to achieve the same functionality as a common current source in parallel with a higher power shorting switch.

Since the voltage across the sensing resistor 144 is proportional to the current the saturable current source 140 sinks, the measure of both the voltage across the sensing resistor 144 and the voltage at the output 146 of the saturable current source 140 enables impedance measurements of the load which is connected to the saturable current source 140 that are based on the ratio of the recorded voltages 146 and 147. It is to be understood that in the preceding description of the impedance measurements it was assumed that the output 146 was connected to grounded tissue. If this is not the case, then the voltage at output 146 is to be replaced by the voltage drop across the stimulated tissue.

Figure 15:
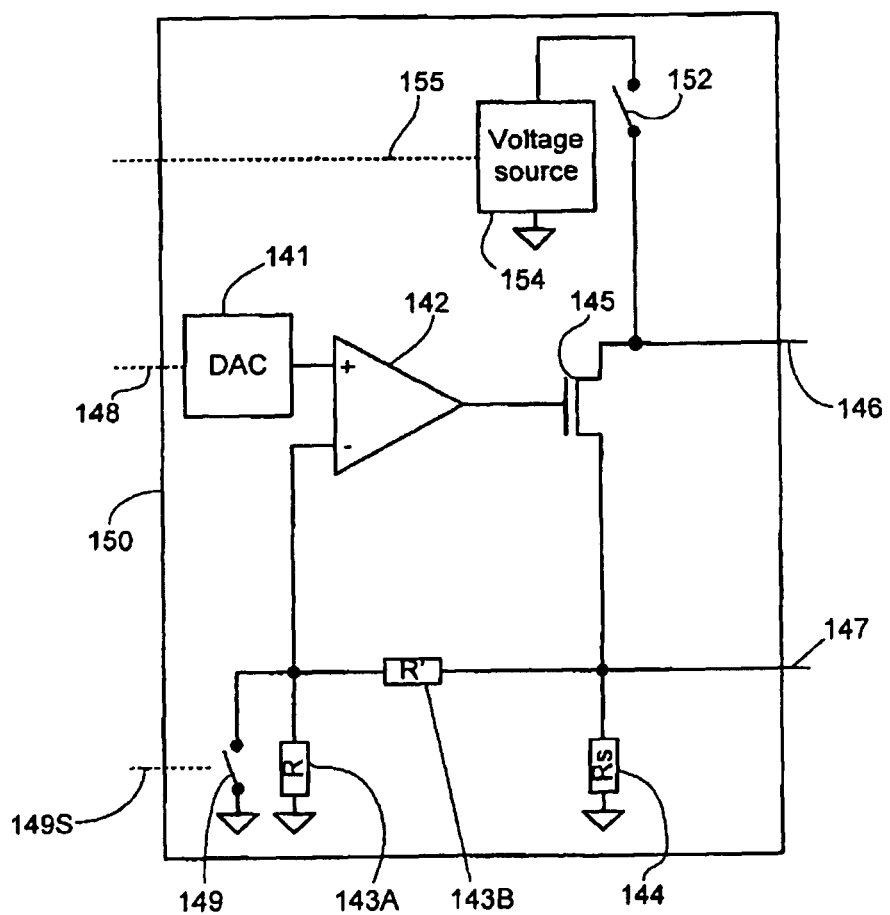
FIG. 15 is a block diagram of a dual-mode source based on the saturable current source of FIG. 14.

Referring to FIG. 15, the saturable current source 140 of FIG. 14 may be connected in parallel with a voltage source 154, controlled by control signal line 155, that may be disconnected using switch 152 when it sinks a controlled current or outputs a controlled voltage, creating a dual-mode source 150. Such a dual-mode source 150 may be used for the dual-mode sources 54, 64A, 64B, 74A, 74B, 84A and 84B of FIGS. 5, 6, 7 and 8. Furthermore, a controlled current flow from the terminal 146 instead of into the terminal 146 may be achieved by using a PMOS transistor or an equivalent circuit for the transistor 145 and connecting the feedback resistors 143A, 143B, the sensing resistor 144 and the switch 149 to the power supply of the circuit.

Since the voltage across the sensing resistor 144 is proportional to the current the dual-mode source 150 sinks, the measure of both the voltage across the sensing resistor 144 and the voltage at the output 146 of the dual-mode source 150 enables impedance measurements of the load which is connected to the dual-mode source 150 that are based on the ratio of the recorded voltages 146 and 147. It is to be understood that in the preceding description of the impedance measurements it was assumed that the output 146 was connected to grounded tissue. If this is not the case, then the voltage at output 146 is to be replaced by the voltage drop across the stimulated tissue.

Figure 16:
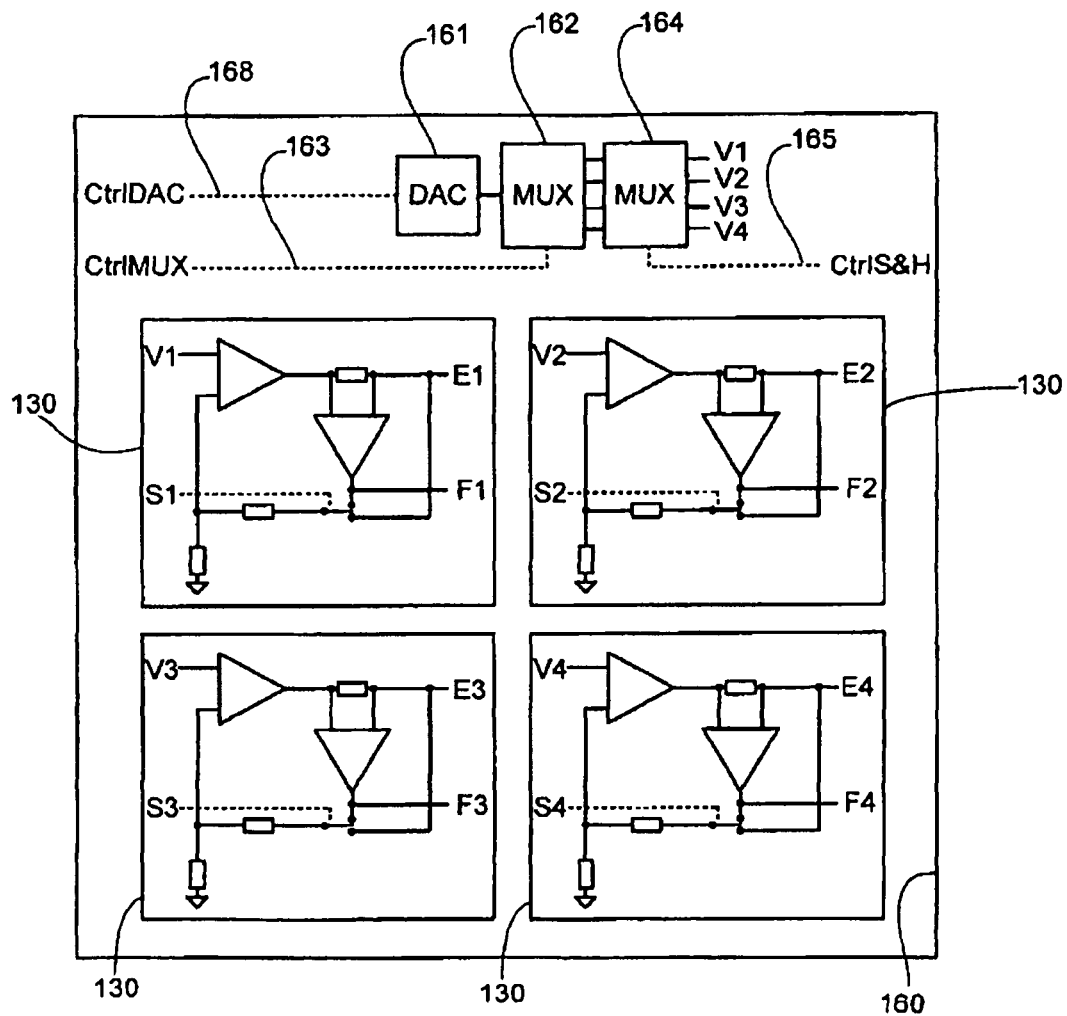
FIG. 16 is a block diagram of a dual-mode source system based on the dual-mode source of FIG. 14.

Referring to FIG. 16, there is shown a block diagram of a dual-mode source system 160 which includes four dual-mode sources 130, as shown in FIG. 13. However, instead of using one DAC 131 per dual-mode source 130, the dual-mode source system 160 may use a single DAC 161, which is coupled to a multiplexer 162 that feeds a multitude of sample-and-hold circuits 164 that each connects to an input V1, V2, V3 and V4 of the dual-mode sources 130. Depending on the commands received from the processing unit 14 of FIG. 1, the control signals S1, S2, S3 and S4 will instruct the dual-mode sources 130 to operate in voltage or current mode when required, whereas control signals CtrlDAC 168, CtrlMUX 163, and CtrlS&H 165 will synchronize the operation of the DAC 161, the multiplexer 162 and the sample-and-hold circuits 164, respectively.

It is to be understood that although the dual-mode source system 160 shown in FIG. 16 includes four dual-mode sources 130, the number of dual-mode sources 130 may vary according to the desired stimulation.

Figure 17:
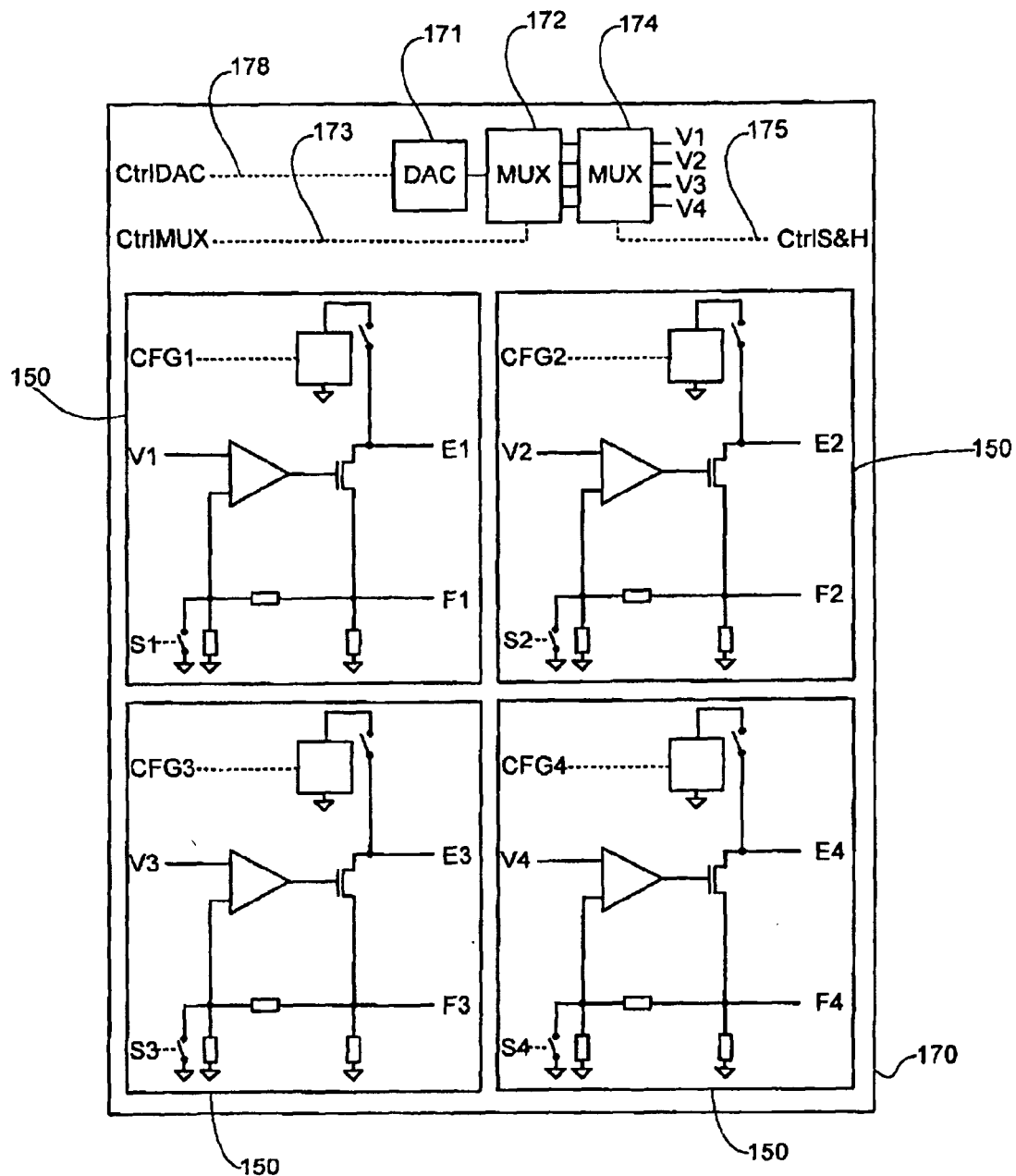
FIG. 17 is a block diagram of a dual-mode source system based on the dual-mode source of FIG. 15.

Referring to FIG. 17, there is shown a block diagram of a dual-mode source system 170 which includes four saturable current source based dual-mode sources 150, as shown in FIG. 15. Again, instead of using one DAC 141 per dual-mode source 150, the dual-mode source system 170 uses a single DAC 171, which is coupled to a multiplexer 172 that feeds a multitude of sample-and-hold circuits 174 that each connects to an input V1, V2, V3 and V4 of the dual-mode sources 150. Depending on the commands received from the processing unit 14 of FIG. 1, the control signals CFG1, CFG2, CFG3, CFG4, S1, S2, S3 and S4 will make the sources operate in voltage, current or saturation mode when required whereas the control signals CtrlDAC 178, CtrlMUX 173, and CtrlS&H 175 will synchronize the operation of the DAC 171, the multiplexer 172 and the sample & hold circuits 174.

It is to be understood that although the dual-mode source system 170 shown in FIG. 17 includes four dual-mode sources 150, the number of dual-mode sources 150 may vary according to the desired stimulation.

Figure 18:
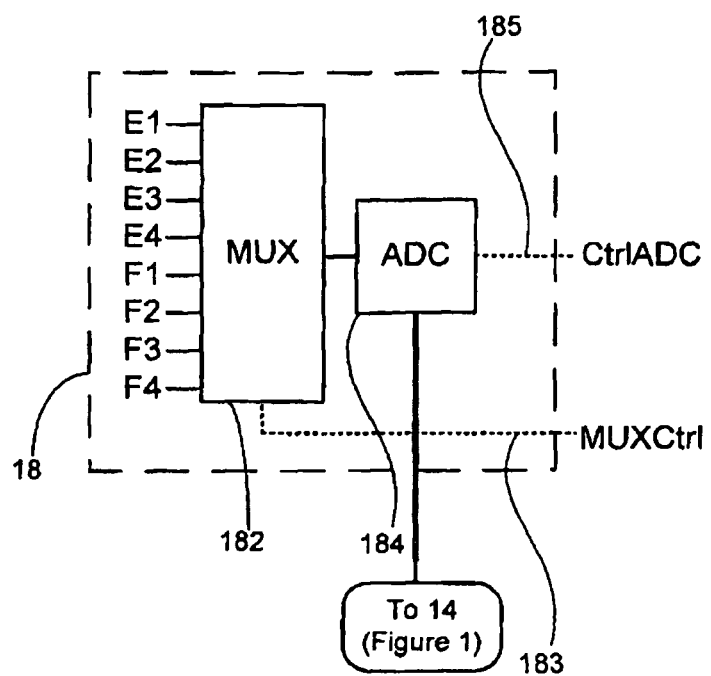
FIG. 18 is a block diagram of the monitoring unit 18 of FIG. 1.

Referring finally to FIG. 18, there is shown a block diagram of a monitoring unit 18 (see FIG. 1) that may be used with the dual-mode source systems 160 and 170 of FIGS. 16 and 17, respectively. The monitoring unit 18 includes a multiplexer 182 connected to the various monitoring points E1, E2, E3, E4, V1, V2, V3 and V4 of FIGS. 16 and 17, and an analog-to-digital converter (ADC) 184 to feed the processing unit 14 (see FIG. 1) and allow the monitoring of the electrical characteristics of the stimulated tissue. As the processing unit 14 samples the monitoring points E1, E2, E3, E4, V1, V2, V3 and V4, using the multiplexer 182 and ADC 184 control signals MUXCtrl 183 and CtrlADC 185, respectively, it may get a voltage value which is proportional to the voltage at the output of the selected dual-mode source 130, 150 or a voltage which is proportional to the current the selected dual-mode source 130, 150 sink or output.

Both the ratio of the voltage at the output of a current source over the current the source sinks and the ratio of the voltage a voltage source outputs over the current through it's sense resistor provide a measure of the impedance of the stimulated tissue.

Although the present invention has been described by way of particular embodiments and examples thereof, it should be noted that it will be apparent to persons skilled in the art that modifications may be applied to the present particular embodiment without departing from the scope of the present invention.

What is claimed is:

1. An implantable pulse generator for providing at least one of a voltage and a current stimulation to a tissue of a subject through at least two electrodes adapted to be in electrical contact with the tissue of the subject, the implantable pulse generator comprising: a stimulation circuit coupled to the at least two electrodes, the stimulation circuit including at least one dual-mode voltage and current source, wherein the stimulation circuit can operate alternatively in a voltage stimulation mode and in a current stimulation mode; and a processing unit coupled to the stimulation circuit, the processing unit being so configured as to control the mode of operation of the stimulation circuit, and wherein the at least one dual-mode voltage and current source includes: an operational amplifier having a positive input, a negative input and an output; a first feedback resistor connected between the negative input of the operational amplifier and a ground; a differential amplifier having a positive input connected to the output of the operational amplifier, a negative input and an output; a sensing resistor connected between the negative and positive inputs of the differential amplifier; a mode selection switch having a first connection connected to the output of the differential amplifier, second connection connected to the negative input of the differential amplifier and a third connection, the mode selection switch being operated by the processing unit; a second feedback resistor connected between the negative input of the operational amplifier and the third connection of the mode selection switch; and a source output connected to the negative input of the differential amplifier; wherein the processing unit causes the mode selection switch to connect the second feedback sensor to the negative input of the differential amplifier when in the voltage stimulation mode and to the output of the differential amplifier when in the current stimulation mode.

2. The implantable pulse generator of claim 1, wherein the positive input of the operational amplifier is connected to the processing unit in order to control the waveform and amplitude of the source output.

3. A dual-mode voltage and current source, comprising: an operational amplifier having a positive input, a negative input and an output; a first feedback resistor connected between the negative input of the operational amplifier and a ground; a differential amplifier having a positive input connected to the output of the operational amplifier, a negative input and an output; a sensing resistor connected between the negative and positive inputs of the differential amplifier; a mode selection switch having a first connection connected to the output of the differential amplifier, second connection connected to the negative input of the differential amplifier and a third connection; a second feedback resistor connected between the negative input of the operational amplifier and the third connection of the mode selection switch; and a source output connected to the negative input of the differential amplifier; wherein a) when the mode selection switch connects the second feedback sensor to the negative input of the differential amplifier, the source output generates a voltage stimulation, and b)

when the mode selection switch connects the second feedback resistor to the output of the differential amplifier, the source output generates a current stimulation.

* * * * *